United States Patent [19]

Shiraki et al.

[11] Patent Number: 5,847,091
[45] Date of Patent: Dec. 8, 1998

[54] FLUORINE-CONTAINING AZO COMPOUNDS

[75] Inventors: Kazuo Shiraki; Nobutaka Shimamura, both of Kawagoe, Japan

[73] Assignee: Wako Pure Chemical Industries, Ltd., Osaka, Japan

[21] Appl. No.: 863,519

[22] Filed: May 27, 1997

[30] Foreign Application Priority Data

May 31, 1996 [JP] Japan ................................. 8-160839

[51] Int. Cl.$^6$ .......................... C07C 245/04; C08F 4/04; C08F 2/00
[52] U.S. Cl. ................ 534/838; 534/886; 424/70.11; 526/219; 526/318.4; 526/346
[58] Field of Search ..................... 534/838, 886; 424/70.11; 526/219, 318.4, 346

[56] References Cited

U.S. PATENT DOCUMENTS

| 3,047,553 | 7/1962 | Coffman | 526/218.1 |
| 3,775,386 | 11/1973 | Citron | 528/28 |
| 4,584,196 | 4/1986 | Vanlerberghe et al. | 424/70 |

FOREIGN PATENT DOCUMENTS 2-167375  6/1990  Japan .

OTHER PUBLICATIONS

*Dispersion Polymerizations in Supercritical Carbon Dioxide,* J.M. DeSimone, E.E. Maugy, Y.Z. Menceloglu, J.B. McClain, T.J. Romack and J. R. Combes, Science vol. 265, 1994, pp. 356–359.

*Synthèse et Caracterisation d'Amorceurs Azoiques Fluorès. Application a l'ètude de la Reaction de Terminaison de Chaine Lors de la Polymèrisation Radicalaire du Styrène,* Jean Marie Bessiere, Bernard Boutevin et Olivier Loubet, Eur. Polym. J. vol. 31, No. 6, pp. 573–580, 1995.

*Primary Examiner*—Fiona T. Powers
*Attorney, Agent, or Firm*—Oliff & Berridge, PLC

[57] ABSTRACT

A fluorine-containing azo compound having a fluorine segment at a molecular terminal is useful as a polymerization initiator for producing, for example, fluorine-containing polymers.

10 Claims, No Drawings

FLUORINE-CONTAINING AZO COMPOUNDS

BACKGROUND OF THE INVENTION

The present invention relates to fluorine-containing azo compounds having a fluorine segment at a molecular terminal, which is useful as, for example, polymerization initiator and the like.

In recent years, polymeric materials have become used in more and more diversified fields, and with this trend, the properties required of polymers are also being diversified. Particularly, polymers having a perfluoroalkylene group (Rf group) in the molecule thereof are noticed with interest because the Rf group part having a low surface free energy is concentrated into the surface region of the polymer to exhibit excellent water-repellency, oil-repellency, heat resistance, weather resistance, slipping characteristics, and the like.

Hitherto, it has been attempted to introduce an Rf group-containing polymer into base material by the method of blending or the like. Such attempts, however, have not exercised a sufficient effect.

Thus, introduction of Rf group into polymer molecule is being attempted by various methods.

For example, a method of introducing Rf group through reaction of a polymer formed by living anionic polymerization with an Rf group-containing alkyl halide has been reported in Polymer Preprints Japan., 44, 948 (1995), etc.

Further, methods for producing a polymer having a fluorine segment by polymerization reaction of a fluorine-containing monomer have also been disclosed. Particularly, a synthesis of block polymer using a monomer having a perfluoroalkylene group is being studied energetically because this method makes it possible to introduce perfluoroalkylene group into molecule in a high efficiency and a high concentration.

However, the method of reacting a polymer with Rf group-containing alkyl halide is limited in the kind of polymer usable, and therefore is low in reactivity. On the other hand, the method of polymerizing a fluorine-containing monomer is disadvantageous in that fluorine segment cannot be introduced into an intended site of polymer molecule and a block polymer cannot be obtained.

As a means for solving the above-mentioned problems, it has been attempted to introduce a fluorine segment through a condensation reaction between a prepolymer having fluorine-containing alkylene group and a polymer.

This method, however, cannot introduce fluorine segment in a high yield because the prepolymer having a fluorine-containing alkylene group is low in solubility.

SUMMARY OF THE INVENTION

In view of above, an object of the present invention is to provide a fluorine-containing azo compound useful for introducing a fluorine segment into an intended site (molecular terminal) of polymer, and a polymer having, in the molecule thereof, a fluorine segment derived from said fluorine-containing azo compound.

The present invention provides a fluorine-containing azo compound represented by the following formula [1]:

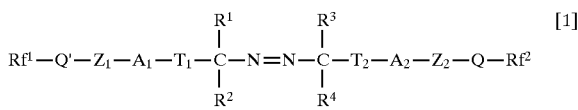

wherein $R^1$ and $R^3$ independently represent a lower alkyl group; $R^2$ and $R^4$ independently represent a lower alkyl group or a cyano group; $A_1$ and $A_2$ independently represent a lower alkylene group which may contain one or more oxygen atoms and/or an aromatic ring; $Z_1$ and $Z_2$ independently represent an ester linkage or an amido linkage; $T_1$ and $T_2$ independently represent —CONH— or a direct link; Q and Q' independently represent a fluorine-containing segment; and $Rf^1$ and $Rf^2$ independently represent a fluorine-containing alkyl group.

The present invention also provides a process for polymerizing a monomer which comprises using the fluorine-containing azo compound mentioned above.

The present invention further provides a polymerization initiator comprising the fluorine-containing azo compound mentioned above.

The present invention still further provides a fluorine-containing polymer containing, as constituents thereof, a unit or units derived from the fluorine-containing azo compound mentioned above and monomer units.

DESCRIPTION OF THE PREFERRED EMBODIMENTS

The fluorine-containing azo compound of the present invention is represented by the following formula [1]:

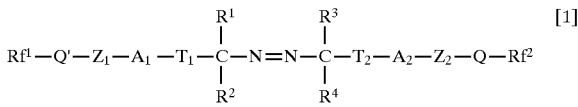

wherein $R^1$ and $R^3$ independently represent a lower alkyl group; $R^2$ and $R^4$ independently represent a lower alkyl group or a cyano group; $A_1$ and $A_2$ independently represent a lower alkylene group which may contain one or more oxygen atoms and/or an aromatic ring; $Z_1$ and $Z_2$ independently represent an ester linkage or an amido linkage; $T_1$ and $T_2$ independently represent —CONH— or a direct link; Q and Q' independently represent a fluorine-containing segment; and $Rf^1$ and $Rf^2$ independently represent a fluorine-containing alkyl group.

In the formula [1], the lower alkyl group represented by $R^1$ to $R^4$ may be linear or branched chain lower alkyl groups of which examples are alkyl groups having 1–6 carbon atoms. Specific examples thereof include a methyl group, an ethyl group, a n-propyl group, an isopropyl group, a n-butyl group, an isobutyl group, a tert-butyl group, a sec-butyl group, a n-pentyl group, an isopentyl group, a neopentyl group, a tert-pentyl group, a 3,3-dimethylbutyl group, a 1,1-dimethylbutyl group, a 1-methylpentyl group, a n-hexyl group, an isohexyl group and the like. The lower alkylene group represented by $A_1$ and $A_2$ which may contain one or more oxygen atoms and/or an aromatic ring is linear or branched chain lower alkylene groups, of which examples are alkylene groups having 1–6 carbon atoms. When said lower alkylene group contains one or more oxygen atoms, lower alkylene groups having —O— group in a number of one or more, preferably 1–5, more preferably 1–3, at one end or both ends of the alkylene group (or chain) or at any position in the alkylene chain can be referred to. When said lower alkylene group has an aromatic ring, lower alkylene groups having an aromatic ring such as a phenylene group, a diphenylene group or the like at one end or both ends or in the alkylene chain can be referred to. Thus, specific examples of said lower alkylene group represented by $A_1$ and $A_2$ include a methylene group, an ethylene group, a propylene group, a butylene group, a 2-methylpropylene group, a pentylene group, a 2,2-dimethylpropylene group, a 2-ethylpropylene group, a hexylene group, a —$CH_2$—$C_6H_4$— group, an o-xylene-α, α'-diyl group, a —O—$CH_2$— group, a —O—$CH_2CH_2$— group, a —$CH_2$—O—$CH_2$— group, a —$CH_2CH_2$—O—$CH_2$ group, a —$CH_2CH_2$—O—$CH_2CH_2$— group, a —$CH_2CH_2$—O—$CH_2CH_2$— group, a —$CH_2$—O—$C_6H_4$— group and the like. As the ester linkage represented by $Z_1$ and $Z_2$, —COO— and —OCO— can be referred to. As the amido linkage represented by $Z_1$ and $Z_2$, —CONH— and —NHCO— can be referred to.

The alkyl group in the fluorine-containing alkyl group represented by $Rf^1$ and $Rf^2$ may be any of linear, branched chain and cyclic alkyl groups, of which examples are alkyl groups having 1—20 carbon atoms. Specific examples thereof include a methyl group, an ethyl group, a n-propyl group, an isopropyl group, a n-butyl group, an isobutyl group, a tert-butyl group, a sec-butyl group, a n-pentyl group, an isopentyl group, a neopentyl group, a tert-pentyl group, a 3,3-dimethylbutyl group, a 1,1-dimethylbutyl group, a 1-methylpentyl group, a n-hexyl group, an isohexyl group, a heptyl group, an octyl group, a nonyl group, a decyl group, an undecyl group, a dodecyl group, a hexadecyl group, an octadecyl group, a cyclopropyl group, a cyclopentyl group, a cyclohexyl group, a 2-cyclohexylethyl group and the like. As the fluorine-containing alkyl group, those obtained by fluorinating hydrogen atom or atoms of the above-mentioned alkyl groups can be referred to, of which examples include a fluoromethyl group, a fluoroethyl group, a fluoropropyl group, a fluorobutyl group, a fluoropentyl group, a fluorohexyl group, a fluoroheptyl group, a fluorooctyl group, a fluorononyl group, a fluorodecyl group, a difluoromethyl group, a difluoroethyl group, a fluorocyclohexyl group, a trifluoromethyl group, a 2-perfluorooctylethyl group, 2,2,2-trifluoroethyl group, a pentafluoroethyl group, a 3,3,4,4,4-pentafluorobutyl group, a perfluoro-n-propyl group, a perfluoroisopropyl group, a perfluoro-n-butyl group, a perfluoroisobutyl group, a perfluoro-tert-butyl group, a perfluoro-sec-butyl group, a perfluoropentyl group, a perfluoroisopentyl group, a perfluoro-tert-pentyl group, a perfluoro-n-hexyl group, a perfluoroisohexyl group, a perfluoroheptyl group, a perfluorooctyl group, a perfluorononyl group, a perfluorodecyl group, a perfluorodecyl group, a perfluorododecyl group, a perfluorooctadecyl group, a perfluorocyclopropyl group, a perfluorocyclopentyl group, a perfluorocyclohexyl group and the like. Of these fluorine-containing alkyl groups, preferred are perfluoroalkyl groups having 1–8 carbon atoms.

As the fluorine-containing segment represented by Q and Q', there can be exemplified fluorine-containing oxyalkylene groups represented by the following formula [2]:

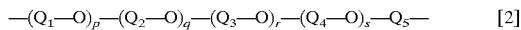

—$(Q_1—O)_p$—$(Q_2—O)_q$—$(Q_3—O)_r$—$(Q_4—O)_s$—$Q_5$—  [2]

wherein $Q_1$ and $Q_4$ independently represent an alkylene group; $Q_2$ and $Q_3$ independently represent a fluorine-containing alkylene group; $Q_5$ represents an alkylene group or a fluorine-containing alkylene group; p and s independently represent 0 or a natural number e.g. 1 to 1000; and q and r independently represent a natural number, e.g., 1 to 1000.

In the formula [2], the alkylene group represented by $Q_1$, $Q_4$ and $Q_5$ may be linear, branched chain and cyclic alkylene groups, of which examples are alkylene groups having 1–10 carbon atoms. Specific examples thereof include a methylene group, an ethylene group, a propylene group, a butylene group, a 2-methylpropylene group, a pentylene group, a 2,2-dimethylpropylene group, a 2-ethylpropylene group, a hexylene group, a heptylene group, an octylene group, a 2-ethylhexylene group, a nonylene group, a decylene group, a cyclopropylene group, a cyclopentylene group, a cyclohexylene group and the like. Of these alkylene groups, lower alkylene groups having 1–6 carbon atoms are preferred. As the fluorine-containing alkylene group represented by Q2, Q3 and Q5, groups obtainable by fluorinating at least one hydrogen atom of the above-mentioned alkylene groups can be referred to, which include those in which hydrogen atoms are wholly fluorinated, too. Examples of said fluorine-containing alkylene groups obtainable by fluorinating one or more hydrogen atoms of the above-mentioned alkylene groups include the following: a fluoromethylene group, a fluoroethylene group, a fluoropropylene group, a fluorobutylene group, a fluoropentylene group, a fluorohexylene group, a difluoromethylene group, a difluoroethylene group, a difluoropropylene group, a trifluoropropylene group, a fluorocyclohexylene group, a trifluoroethylene group, a pentafluoroethylene group, a perfluoropropylene group, a perfluoro-2,2-dimethylpropylene group, a perfluoro-2-ethylpropylene group, a perfluorohexylene group, a perfluorocyclopropylene group, a perfluorocyclopentylene group, a perfluorocyclohexylene group and the like. Of these fluorine-containing alkylene groups, preferred are perfluoroalkylene groups having 1–6 carbon atoms.

Molecular weight of the fluorine-containing segment is appropriately selected usually from a range of 100–50,000, preferably from a range of 500–25,000 and more preferably from a range of 1,000–10,000.

The fluorine-containing azo compound of the present invention represented by the above-mentioned formula [1] can be produced, for example, in the following manner.

That is, for example, an azo compound represented by the following formula [3]:

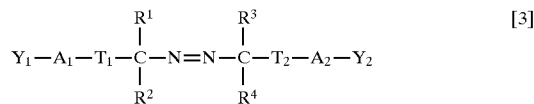

is reacted with a fluorine-containing compound which has terminal groups reactive with $Y_1$ and $Y_3$, e.g. a fluorine-containing ether compound represented by the following formula [4]:

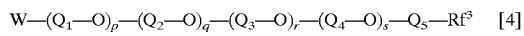

W—$(Q_1—O)_p$—$(Q_2—O)_q$—$(Q_3—O)_r$—$(Q_4—O)_s$—$Q_5$—$Rf^3$  [4]

in an appropriate solvent, if desired in the presence of a basic catalyst, by the use of a dehydrating agent, and optionally in an inert gas atmosphere, whereby the fluorine-containing azo compound [1] can be obtained.

In the formulae [3] and [4], $R^1$ to $R^4$, $A_1$, $A_2$, $T_1$, $T_2$, $Q_1$ to $Q_5$, p, q, r and s are as defined above, and $Rf^3$ represents a fluorine-containing alkyl group. $Y_1$ and $Y_2$ represent independently a carboxyl group, a hydroxyl group, an amino group or an isocyanate group; and W represents a group reactive with $Y_1$ and $Y_2$ to form an ester linkage or an amido linkage. Thus, $Y_1$, $Y_2$ and W form a combination of groups which can mutually react to form an ester linkage or an amido linkage. For example, there can be a case that one of the groups is a carboxyl group and the other is a hydroxyl group or an amino group; a case that one of the groups is a hydroxyl group and the other is a carboxyl group or an isocyanato group; a case that one is an amino group and the other is a carboxyl group; a case that one is an isocyanto group and the other is a hydroxyl group, etc.

As examples of the fluorine-containing alkyl group represented by $Rf^3$ in the formula [3], the same ones as those represented by $Rf^1$ and $Rf^2$ in the formula [1] can be referred to.

As the reaction solvent, for example, ethers such as diethyl ether, diisopropyl ether, tetrahydrofuran, dioxane, dimethoxyethane and the like, halogenated hydrocarbons such as carbon tetrachloride, chloroform, methylene chloride, dichloroethane, trichloroethylene, xylene hexafluoride and the like, hydrocarbons such as n-hexane, benzene, toluene, xylene and the like, esters such as methyl acetate, ethyl acetate, butyl acetate, methyl propionate and the like, acetonitrile, N,N-dimethylformamide and the like can be referred to. These solvents may be used singly or as a mixture thereof.

As the dehydrating agent, the substances usable as a dehydrating-condensing agent can be used without limitation. Examples thereof include inorganic dehydrating agents such as concentrated sulfuric acid, diphosphorus pentoxide, anhydrous zinc chloride and the like; carbodiimides such as dicyclohexyl carbodiimide, diisopropyl carbodiimide, 1-ethyl-3-(3-dimethylaminopropyl-carbodiimide) hydrochloride and the like; polyphosphoric acid, acetic anhydride, carbonyldiimidazole, p-toluenesulfonyl chloride and the like.

The amount of the dehydrating agent is not particularly limited. However, too small an amount of dehydrating agent makes the progress of reaction too slow, and too large an amount of the dehydrating agent deteriorates economy of the process. Accordingly, the dehydrating agent is used usually in an amount of 1–5 moles and preferably in an amount of 2–3 moles, per mole of the azo compound or the fluorine-containing ether compound.

The production mentioned above is preferably put into practice in the presence of a basic catalyst. Concrete examples of said basic catalyst include organic amines such as triethylamine, diisopropylethylamine, N,N-dimethylaniline, piperidine, pyridine, 4-dimethylaminopyridine, 1,5-diazabicyclo[4.3.0]nona-5-ene, 1,8-diazabicyclo[5.4.0]undec-7-ene, tri-n-butylamine, N-methylmorpholine and the like; metal hydrides such as sodium hydride and the like; and basic alkali metal compounds such as n-butyllithium, tert-butyllithium and the like.

The basic catalyst is used usually in an amount of 0.5–5 moles and preferably in an amount of 1–2 moles, per mole of the azo compound or the dehydrating agent.

In the production of the fluorine-containing azo compound of the present invention, the ratio of the fluorine-containing ether compound to the azo compound is not particularly limited but it may be decided appropriately. The fluorine-containing ether compound is used usually in an amount of 1.5–5 moles and preferably in an amount of 2–3 moles per mole of the azo compound.

The reaction can be carried out in an inert gas atmosphere. Examples of the inert gas are a nitrogen gas, an argon gas and the like.

The reaction temperature is not particularly limited. However, too high a reaction temperature causes a decomposition of the azo group and too low a reaction temperature reduces the reaction velocity and makes the reaction take a long period of time. Accordingly, the reaction temperature is usually selected from a temperature range of from −10° C. to 60° C. appropriately. If desired, the reaction temperature may be elevated stepwise from a low temperature. The reaction time may vary depending on other reaction conditions, and is usually selected from a range of 1–60 hours appropriately.

The objective product is isolated by an appropriate means in accordance with the kinds and amounts of starting materials, basic catalyst, dehydrating agent and solvent and the state of reaction mixture. For example, when the reaction mixture is a viscous liquid, the reaction mixture is diluted with an appropriate solvent and then the impurities are removed by the method of filtration or washing with water, after which the solvent is removed. In this manner, the objective fluorine-containing azo compound can be obtained.

As the azo compound represented by the formula [3] and the fluorine-containing ether compound represented by formula [4] used as starting materials, any of commercial products and home-made products appropriately prepared by conventional methods may be used. The fluorine-containing ether compound represented by formula [4] may be any of single compound and an appropriate combination of two compounds.

Since the fluorine-containing azo compound thus obtained easily generate radical species with evolution of nitrogen gas by cleavage of azo groups upon heating or photo-irradiation, polymerization proceeds rapidly even if any of various monomers are present together with the fluorine-containing azo compound.

Using the fluorine-containing azo compound of the present invention as a polymerization initiator, a monomer can be polymerized or copolymerized, for example, in the following manner.

That is, the fluorine-containing azo compound obtained in the above-mentioned manner and a monomer represented by the following formula [5]:

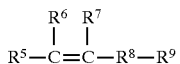

[5]

are subjected to a conventional polymerization in an appropriate solvent or in the absence of solvent, and if desired in an atmosphere of an inert gas.

In the formula [5], $R^5$ represents a hydrogen atom, a lower alkyl group or a halogen atom; $R^6$ represents a hydrogen atom, a lower alkyl group, a halogen atom, a carboxyl group, an alkyloxycarbonyl group or a formyl group; $R^7$ represents a hydrogen atom, a lower alkyl group, a carboxyl group, an alkyloxycarbonyl group or a halogen atom; $R^8$ represents an alkylene group which may optionally have a double bond or represents a direct link; and $R^9$ represents a hydrogen atom, an alkyl group, a haloalkyl group, an aryl group, an aliphatic heterocyclic group, an aromatic heterocyclic group, a halogen atom, an alkyloxycarbonyl group, an aralkyloxycarbonyl group, a hydroxyalkyloxycarbonyl group, an aryloxycarbonyl group, an acyloxy group, a cyano group, a carboxyl group, a formyl group, an amino group, a sulfonic acid group, a carbamoyl group or a hydroxyl group.

The treatment after the reaction may be according to the conventional treatments employed in this field of the art.

If desired, a chain transfer agent such as laurylmercaptan, octylmercaptan, butylmercaptan, 2-mercaptoethanol, butyl thioglycolate or the like may be added at the time of carrying out the polymerization reaction in order to control the molecular weight.

Conventional polymerization methods such as suspension polymerization, solution polymerization, bulk polymerization, emulsion polymerization, etc. can be used in the present invention. In these polymerization methods, the fluorine-containing azo compound may be used in combination with a conventional radical polymerization initiator such as azobisisobutyronitrile, dimethyl 2,2'-azobisisobutyrate or the like.

The monomer of the formula [5] is explained in more detail.

In the formula [5], as the halogen atoms represented by $R^5$, $R^6$, $R^7$ and $R^8$, fluorine, chlorine, bromine, iodine and the like can be referred to. The lower alkyl group represented by $R^5$, $R^6$ and $R^7$ may be linear or branched chain lower alkyl groups, of which examples are alkyl groups having 1–6 carbon atoms. Specific examples thereof include a methyl group, an ethyl group, a n-propyl group, an isopropyl group, a n-butyl group, an isobutyl group, a tert-butyl group, a sec-butyl group, a n-pentyl group, an isopentyl group, a neopentyl group, a n-tert-pentyl group, a 3,3-dimethylbutyl group, a 1,1-dimethylbutyl group, a 1-methylpentyl group, a n-hexyl group, an isohexyl group and the like. The alkyloxycarbonyl group represented by $R^6$, $R^7$ and $R^9$ may be any of straight chain and branched chain alkyloxycarbonyl groups, and may have a double bond if desired. For example, alkyloxycarbonyl groups having 2–19 carbon atoms can be referred to. Specific examples thereof include a methyloxycarbonyl group, an ethyloxycarbonyl group, a propyloxycarbonyl group, a butyloxycarbonyl group, a pentyloxycarbonyl group, a hexyloxycarbonyl group, a heptyloxycarbonyl group, an octyloxycarbonyl group, a dodecyloxycarbonyl group, an octadecyloxycarbonyl group, an ethenyloxycarbonyl group, a propenyloxycarbonyl group, a butenyloxycarbonyl group, a tert-butyloxycarbonyl group, a 2-ethylhexyloxycarbonyl group and the like. The alkyl group represented by $R^9$ may be linear, branched chain or cyclic alkyl groups, and may have a double bond if desired. For example, alkyl groups having 1–20 carbon atoms can be referred to. Specific examples thereof include a methyl group, an ethyl group, a n-propyl group, an isopropyl group, a n-butyl group, an isobutyl group, a tert-butyl group, a sec-butyl group, a n-pentyl group, an isopentyl group, a neopentyl group, a tert-pentyl group, a 3,3-dimethylbutyl group, a 1,1-dimethylbutyl group, a 1-methylpentyl group, a n-hexyl group, an isohexyl group, a heptyl group, an octyl group, a nonyl group, a decyl group, an undecyl group, a dodecyl group, a hexadecyl group, an octadecyl group, a cyclopropyl group, a cyclopentyl group, a cyclohexyl group, an ethenyl group, a propenyl group, a butenyl group, a pentenyl group, a hexenyl group, a heptenyl group, an octenyl group and the like. As the haloalkyl group, haloalkyl groups having 1–20 carbon atoms obtained by halogenating (for example, fluorinating, chlorinating, brominating, iodinating, etc.) the above-mentioned alkyl groups can be referred to. Specific examples thereof include a chloromethyl group, a bromomethyl group, a trifluoromethyl group, a 2-chloroethyl group, a 3-chloropropyl group, a 3-bromopropyl group, a 3,3,3-trifluoropropyl group, a 2-perfluorooctylethyl group, a perfluorooctyl group, a 1-chlorodecyl group, a 1-chlorooctadecyl group and the like. As said aryl group, a phenyl group, a tolyl group, a xylyl group, a naphthyl group, an anthryl group, a 4-methylphenyl group, a 4-ethylphenyl group, a 4-methoxyphenyl group, a 4-vinylphenyl group, a 4-chlorophenyl group, an aminophenyl group, a hydroxyphenyl group, a carboxyphenyl group and the like can be referred to. As said aliphatic heterocyclic group, for example, 5-membered and 6-membered aliphatic heterocyclic groups are preferable, and those containing 1–3 hetero atoms such as nitrogen atom, oxygen atom, sulfur atom and the like can be referred to. Specific examples thereof include a pyrrolidyl-2-one group, a piperidino group, a piperazinyl group, a morpholino group and the like. As said aromatic heterocyclic group, for example, 5-membered and 6-membered aromatic heterocyclic groups are preferable, and those containing 1–3 hetero atoms such as nitrogen atom, oxygen atom, sulfur atom or the like can be referred to. Specific examples thereof include a pyridyl group, an imidazolyl group, a thiazolyl group, a furanyl group, a pyranyl group and the like. As said aralkyloxycarbonyl group, for example, aralkyloxycarbonyl groups having 8–20 carbon atoms can be referred to. Specific examples thereof include a benzyloxycarbonyl group, a phenethyloxycarbonyl group and the like. As said acyloxy group, acyloxy groups having 2–18 carbon atoms derived from carboxylic acids can be referred to. Specific examples thereof include an acetyloxy group, a propionyloxy group, a butyryloxy group, a pentanoyloxy group, a hexanoyloxy group, a heptanoyloxy group, an octanoyloxy group, a lauroyloxy group, a stearoyloxy group, a benzoyloxy group and the like. As said hydroxyalkyloxycarbonyl group, hydroxyalkyloxycarbonyl groups having 2–19 carbon atoms obtained by replacing the hydrogen atom in the above-mentioned alkyloxycarbonyl groups with a hydroxyl group can be referred to. Specific examples thereof include a hydroxymethyloxycarbonyl group, a hydroxyethyloxycarbonyl group, a hydroxypropyloxycarbonyl group, a hydroxybutyloxycarbonyl group, a hydroxypentyloxycarbonyl group, a hydroxyhexyloxycarbonyl group, a hydroxyheptyloxycarbonyl group, a hydroxyoctyloxycarbonyl group, a hydroxydodecyloxycarbonyl group, a hydroxy-octadecyloxycarbonyl group and the like. As said aryloxycarbonyl group, for example, aryloxycarbonyl groups having 7–20 carbon atoms can be referred to. Specific examples thereof include a phenyloxycarbonyl group, a naphthyloxycarbonyl group and the like. The alkylene group represented by $R^8$, which may have a double bond if desired, may be linear or branched chain alkylene groups, and examples thereof are alkylene groups having 1–10 carbon atoms. When said alkylene group has a double bond, examples of such alkylene group include alkylene groups having double bond at an arbitrary position of the chain in a number of one or more, preferably 1–5 and further preferably 1–3. Specific examples thereof include a methylene group, an ethylene group, a propylene group, a butylene group, a 2-methylpropylene group, a pentylene group, a 2,2-dimethylpropylene group, a 2-ethylpropylene group, a hexylene group, a heptylene group, an octylene group, a 2-ethylhexylene group, a nonylene group, a decylene group, an ethenylene group, a propenylene group, a butenylene group, a pentenylene group, a hexenylene group, a butadienylene group and the like, though the invention is by no means limited by these examples.

Specific examples of the monomers which can be used in the production of the fluorine-containing polymer of the present invention are as follows:

ethylenic aromatic hydrocarbons having 8–20 carbon atoms such as styrene, 4-methylstyrene, 4-ethylstyrene, 4-methoxystyrene, divinylbenzene and the like;

vinyl esters having 3–20 carbon atoms such as vinyl formate, vinyl acetate, vinyl propionate, isopropenyl acetate and the like;

halogen-containing vinyl compounds having 2–20 carbon atoms such as vinyl chloride, vinylidene chloride, vinylidene fluoride, tetrafluoroethylene, tetrachloroethylene and the like;

ethylenic carboxylic acids having 3–20 carbon atoms such as acrylic acid, methacrylic acid, itaconic acid, maleic acid, fumaric acid, crotonic acid, citraconic acid, methaconic acid, vinylacetic acid, allylacetic acid, vinylbenzoic acid and the like (if desired, these acids may be in the form of a salt such as alkali metal salt including sodium salt and potassium salt or in the form of ammonium salt);

esters of ethylenic carboxylic acids having 4–20 carbon atoms such as methyl methacrylate, ethyl methacrylate, propyl methacrylate, butyl methacrylate, 2-ethylhexyl methacrylate, lauryl methacrylate, stearyl methacrylate, vinyl methacrylate, allyl methacrylate, phenyl methacrylate, benzyl methacrylate, methyl acrylate, ethyl acrylate, butyl acrylate, 2-ethylhexyl acrylate, lauryl acrylate, stearyl acrylate, vinyl acrylate, dimethyl itaconate, diethyl itaconate, dimethyl maleate, diethyl maleate, dimethyl fumarate, diethyl fumarate, methyl crotonate, ethyl crotonate, vinyl crotonate, dimethyl citraconate, diethyl citraconate, dimethyl methaconate, diethyl methaconate, methyl 3-butenoate, 2-hydroxyethyl methacrylate, 3-hydroxypropyl methacrylate, 2-hydroxypropyl methacrylate, 2-hydroxyethyl acrylate, 3-hydroxypropyl acrylate, 2-hydroxypropyl acrylate and the like;

cyano-containing vinyl compounds having 3–20 carbon atoms such as acrylonitrile, methacrylonitrile, allyl cyanide and the like;

vinylamide compounds having 3–20 carbon atoms such as acrylamide, methacrylamide and the like;

ethylenic aldehydes having 3–20 carbon atoms such as acrolein, crotonaldehyde and the like;

vinylsulfonic acids having 2–20 carbon atoms such as vinylsulfonic acid, 4-vinylbenzenesulfonic acid and the like (if desired, these acids may be in the form of a salt such as alkali metal salt including sodium salt, potassium salt and the like);

vinyl type aliphatic amines having 2–20 carbon atoms such as vinylamine, allylamine and the like;

vinyl type aromatic amines having 8–20 carbon atoms such as vinylaniline and the like;

vinyl type aliphatic heterocyclic amines having 5–20 carbon atoms such as N-vinylpyrrolidone, vinylpiperidine and the like;

vinyl type aromatic heterocyclic amines having 5–20 carbon atoms such as vinylpyridine, 1-vinylimidazole and the like;

ethylenic alcohols having 3–20 carbon atoms such as allyl alcohol, crotyl alcohol and the like;

ethylenic phenols having 8–20 carbon atoms such as 4-vinylphenol and the like;

diene compounds having 4–20 carbon atoms such as butadiene, isoprene and the like; etc.

These monomers may be used either singly or in proper combination thereof.

In the fluorine-containing polymer of the present invention obtained by polymerizing monomers in the presence of the fluorine-containing azo compound of the present invention, the constitutional percentage of the unit or units derived from the fluorine-containing azo compound is not particularly limited, but may be appropriately selected usually from a range of 1–99% by weight, preferably from a range of 5–95% by weight, and more preferably from a range of 10–90% by weight.

The constitutional percentages of the monomer units are not particularly limited, but the percentages may be selected usually from a range of 99–1% by weight, preferably from a range of 95–5% by weight, and more preferably from a range of 90–10% by weight.

The concentrations of the fluorine-containing azo compound and the monomers at the time of polymerization are properly chosen so as to adjust the total concentrations of these components in the polymerization solution usually 5% (solvent 95%) to 100% by weight (in the absence of solvent), preferably 10–100% by weight.

The polymerization is preferably carried out in the presence of an organic solvent. The organic solvents which can be used include, for example, hydrocarbons such as toluene, xylene, benzene, cyclohexane, n-hexane, n-octane and the like; halogenated hydrocarbons such as methylene chloride, chloroform, carbon tetrachloride, dichloroethane, trichloroethane, xylene hexafluoride and the like; esters such as methyl acetate, ethyl acetate, n-butyl acetate, methyl propionate and the like; carboxylic acids such as fluoroacetic acid, trifluoroacetic acid, trifluoroacetic acid anhydride and the like; ketones such as acetone, methyl ethyl ketone, cyclohexanone and the like; cyclic ethers such as tetrahydrofuran, dioxane and the like; alcohols such as methanol, ethanol n-propanol, isopropanol, n-butanol, isobutanol, tert-butanol and the like; and N-methylpyrrolidone, N,N-dimethylacetamide, dimethyl sulfoxide and the like. These organic solvents may be used singly or as a mixture thereof. When the fluorine-containing polymer of the present invention is used as a base material for cosmetic, the use of an alcohol such as ethanol, isopropanol or the like as a solvent in the polymerization is preferable because the residual solvent exercises no influence on human body and the fluorine-containing polymer formed by reaction can directly be used as a base material for cosmetic.

The polymerization is preferably carried out in an atmosphere of an inert gas. As said inert gas, for example, nitrogen gas, argon gas and the like can be used.

The temperature of polymerization is not particularly limited. However, when the temperature is too low, the extent of decomposition of azo group is small so that the polymerization progresses too slowly; and when the temperature is too high, an excessive decomposition of azo group takes place so that the polymerization is difficult to control. Accordingly, the temperature of polymerization is appropriately selected usually from a range of 20°–150° C. and preferably from a range of 40°–120° C. The reaction time may vary depending on the reaction temperature, the kinds and concentrations of fluorine-containing azo compound and monomers and other reaction conditions, and may be appropriately selected usually from a range of 2–24 hours.

Molecular weight of the fluorine-containing polymer thus obtained is not particularly limited. As expressed in terms of number average molecular weight, however, the molecular weight is usually 3,000 or more, preferably 5,000 to 2,000,000, and more preferably 10,000 to 1,500,000.

The content of fluorine in the fluorine-containing polymer is appropriately selected usually from a range of 0.1–90%, and preferably from a range of 1–75%.

Since high molecular compounds generally have complicated structures, the structure thereof cannot always be expressed by a single formula. If the fluorine-containing polymer of the present invention is daringly expressed by a structural formula, the polymer may be expressed by, for example, the formula [6] mentioned below, because the polymerization is carried out by using a fluorine-containing azo compound of general formula [1] having fluorine-containing segments on both molecular terminals thereof as a polymerization initiator. Needless to say, the structural formula presented herein is not limitative:

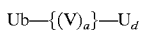  [6]

wherein U represents a fluorine-containing unit; V represents a monomer unit; "a" represents a natural number; and b and d independently represent 0 or an integer of 1, provided that when b is 0, d is an integer of 1, and when d is 0, b is an integer of 1; and { } embraces a random structure including various structures such as graft copolymer structure, block copolymer structure, etc.

In the fluorine-containing polymer of the formula [6], the unit derived from the fluorine containing azo compound is represented by the formula [1a] or [1b]:

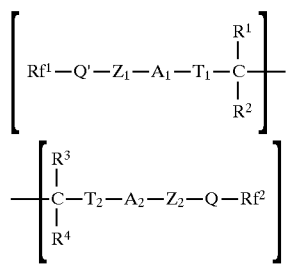

or both the formulae [1a] and [1] in the case of two units being present.

In the formulae [1a] and [1b], $R^1$ through $R^4$, $A_1$, $A_2$, $Z_1$, $Z_2$, $T_1$, $T_2$, Q, Q', $Rf^1$ and $Rf^2$ are as defined above.

The monomer unit V derived from the monomer of the formula [5] can be represented by the following formula:

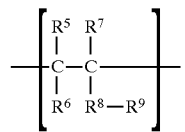

wherein $R^5$ through $R^9$ are as defined above.

The fluorine-containing polymer thus obtained exhibits excellent effects in water-repellency, oil-repellency, heat resistance, weather resistance, chemical resistance, dust-proofing property, adhesive property, etc., and therefore is expected to be useful as a polymer for resin compositions such as painting resin compositions, coating resin compositions and the like, or as a base material for cosmetics such as hair cosmetics (e.g. hair setting agent, hair treatment agent, etc.), fundamental cosmetic and the like, or as many other agents such as mold release agent, coating agent, surface modifier, medical therapeutic material, anti-adhesion agent, deodorant, etc.

When the monomer used in the fluorine-containing polymer is a water-soluble compound, the fluorine-containing polymer obtained therefrom can be water-soluble and therefore can effectively be used as a water-soluble paint or the like. When the monomer is an oil-soluble compound, the fluorine-containing polymer obtained therefrom is high in water-repellency and therefore is effectively usable as an oil-soluble coating material or the like.

When the fluorine-containing polymer of the present invention is used as a polymer for resin compositions for use as a paint or a coating material, the solvents which can be used in the composition include, for example, aromatic hydrocarbons such as benzene, toluene, xylene and the like, ketones such as acetone, methyl ethyl ketone and the like, ethers such as diethyl ether, diisopropyl ether, tetrahydrofuran, dioxane, dimethoxyethane and the like, lower alcohols such as methanol, ethanol, n-propanol, isopropanol, butanol, sec-butanol and the like, esters such as ethyl acetate, butyl acetate, methyl propionate and the like, etc.

When the fluorine-containing polymer of the present invention is put to use in the form of the above-mentioned resin compositions, other components may be added thereto, if necessary. The components which may be added include one or more pigments, fillers, aggregates, anti-foaming agents, plasticizers, anti-rusting agents, film-forming assistants, ultraviolet absorbers, thickness, mold release agents, dyes, and the like, though these are not limitative.

Some of the fluorine-containing polymers of the present invention are excellent in solubility in water and ethanol, and have a possibility of exhibiting excellent functions necessary for a base material for hair cosmetics, such as moisture resistance, setting ability, elasticity, flaking property, feeling, etc. when used as a base material for hair cosmetics.

When the fluorine-containing polymer of the present invention is dissolved in a hydrophilic organic solvent and used as a base material for cosmetic compositions, the hydrophilic organic solvent can be selected from lower alcohols and glymes. Of these hydrophilic organic solvents, preferred are ethanol, isopropanol and the like from the viewpoint of influence on human body.

When the fluorine-containing polymer of the present invention is used as a base material for cosmetics, other cosmetic components may be added so long as addition of such other components does not damage the function of the polymer. Non-limitative examples of the components which may be added include one or more surfactants, fats and oils, sugars, acids, bases, buffers, salts, water, alcohols, protein derivatives, crude drugs, propellants, antiseptic bactericides, antioxidants, ultraviolet absorbers, sequestering agents, oxidizing agents, reducing agents, dyes, perfumes, and the like.

The fluorine-containing polymer of the present invention is characterized in that, since monomer is polymerized in the presence of a fluorine-compound azo compound having fluorine segments on both molecular terminals thereof, fluorine segments are introduced into molecular terminals of the polymer. Thus, according to the present invention, a fluorine segment can be introduced selectively into the molecular terminal of polymer, whereas it has been difficult according to prior arts to introduce a fluorine segment into an intended position of molecule.

Further, when the fluorine segment has a high fluorine content, the fluorine-containing polymer obtained therefrom is a block polymer.

Next, the present invention is explained in more detail by referring to Examples and Experimental Examples. The invention is by no means limited by these Examples.

EXAMPLE 1

In a solvent mixture comprising 66 ml of m-xylene hexafluoride and 30 ml of methylene chloride were suspended 43.7 g of MF-403(trade name of a product manufactured by Garden Co.; fluorinated polyoxyalkylene having a hydroxyl group on one molecular terminal; weight average molecular weight ca. 1,450), 13.6 g of dicyclohexyl carbodiimide (DCC), 2.0 g of 4-dimethyl-aminopyridine (DMAP) and 9.3 g of 4,4"-azobis(4-cyanopentanoic acid). The reaction was carried out at 20°–25° C. for 8 hours with stirring. After allowed to stand overnight, deposited crystals were filtered off and the solvent was distilled off from the filtrate under reduced pressure. Then, 500 ml of methanol was added to the residue to precipitate a fluorine-containing azo compound. The precipitate was collected by filtration and dried under reduced pressure to obtain 22.6 g (yield 45.2%) of the objective fluorine-containing azo compound.
$^1$H-NMR δppm (CDCl$_3$): 1.67 (s, 3H, CH$_3$), 1.72 (s, 3H, CH$_3$), 2.35–2.6 (m, 8H, N—C—CH$_2$CH$_2$—CO), 3.65–3.85 (m, 8H, COO—CH$_2$CH$_2$O, O—CH$_2$CF$_2$), 4.27(brs, 4H, COO—CH$_2$CH$_2$)
IR: 1740 cm$^{-1}$ (COO), 1240 cm$^{-1}$ (—CF$_2$—).

EXAMPLE 2

Into 60 ml of m-xylene hexafluoride were mixed 5.0 g of the fluorine-containing azo compound obtained in Example 1 and 20 g of methyl methacrylate (herein-after simply referred to as MMA), and then subjected to polymerization at 70° C. for 5 hours under a nitrogen stream. After the reaction, the reaction mixture was poured into one liter of methanol to precipitate a fluorine-containing polymer. The polymer was collected by filtration and dried. Thus, 10.1 g (yield 40.6%) of the objective fluorine-containing polymer was obtained as a light yellow-colored bulky product. A GPC measurement revealed that number average molecular weight of this product was 23,800, the weight average molecular weight thereof was 36,700, and the product was a fluorine-containing polymer having a degree of dispersion of 1.54. Hereinafter, this product is called "Polymer F1".

EXAMPLE 3

Polymerization was carried out just in the same manner as in Example 2, except that styrene was used in place of MMA. As a result, 11.8 g (yield 47.1%) of the objective fluorine-containing polymer was obtained as a light yellow powdery product. A GPC chromatographic measurement revealed that number average molecular weight and weight average molecular weight of the product were 15,500 and 25,900, respectively, and the degree of dispersion was 1.67. Hereinafter, this product is called "Polymer F2".

EXPERIMENTAL EXAMPLE 1

One gram of Polymer F2 obtained in Example 2 was taken into a measuring flask. By adding chloroform, the polymer was dissolved, and the total volume was adjusted to 10 ml. Then, the solution thus obtained was cast on a glass dish to form a film. The film was dried under reduced pressure, and the contact angle with water was measured by means of FACE CONTACT-ANGLE METER CA-D (manufactured by Kyowa Interface Science Co., Ltd.). The results are shown in Table 1.

EXPERIMENTAL EXAMPLE 2

A film was prepared by casting just in the same manner as in Experiment Example 1, except that Polymer F2 was used in place of Polymer F1, and contact angle with water was measured. The results are shown in Table 1.

Comparative Example 1

Polymerization was carried out in the same manner as in Example 2, except that 0.14 g of azobisisobutyronitrile (AIBN) was used in place of the 1.0 g of fluorine-containing azo compound obtained in Example 1. As a result, 43.7 g (yield 43.6%) of polymethyl methacrylate (hereinafter referred to as PMMA) was obtained as a white-colored bulky product. A GPC measurement revealed that number average molecular weight and weight average molecular weight of the product were 68,000 and 121,000, respectively, and the degree of dispersion was 1.77.

One gram of the PMMA thus obtained was taken into a measuring flask, and chloroform was added to dissolve the PMMA and adjust the total volume to 10 ml . The solution thus obtained was cast on a glass dish to form a film, and the contact angle with water was measured by means of FACE CONTACT-ANGLE METER CA-D (manufactured by Kyowa Interface Science Co., Ltd.).

The results are shown in Table 1.

TABLE 1

| Example No. | Contact angle with water (°) Film surface (Air side) | Film-formability[1] |
|---|---|---|
| Experimental Example 1 | 108.3 | Good |
| Experimental Example 2 | 109.4 | Good |
| Comparative Example 1 | 74.3 | Good |

[1]Film-formability was evaluated by visually checking whether or not a uniform film was formed on the surface in each dish.

It is apparent from the results mentioned above that both the films obtained in Experiment Examples 1 and 2 obtained by casting the fluorine-containing polymers of the present invention are greater in contact angle with water and higher in water-repellency than the film of Comparative Example 1 obtained by casting PMMA, and therefore the fluorine-containing polymer of the present invention is explicitly superior to PMMA when used as a polymer for a resin composition such as paint and the like or as a base material for cosmetics.

EXPERIMENTAL EXAMPLE 3

Solubility Test

Polymer F1 obtained in Example 2 and Polymer F2 obtained in Example 3 were separately taken into measuring flasks. By adding a variety of solvents thereto, solubilities of the samples were tested. The results are shown in Table 2.

TABLE 2

| Solvent | Polymer F1 | Polymer F2 |
|---|---|---|
| Acetone | Soluble | Soluble |
| MEK[1] | Soluble | Soluble |
| Chloroform | Soluble | Soluble |
| Methylene chloride | Soluble | Soluble |
| Ethyl acetate | Soluble | Soluble |
| Toluene | Soluble | Soluble |
| HFIP[2] | Soluble | Inoluble |
| Ph(CF$_3$)$_2$[3] | Swellable | Soluble |
| n-Hexane | Insoluble | Insoluble |
| Methanol | Insoluble | Insoluble |
| THF[4] | Soluble | Soluble |

[1]MEK: Methyl ethyl ketone
[2]HFIP; Hexafluoroisopropanol
[3]Ph(CF$_3$)$_2$: Xylene hexafluoride
[4]THF: Tetrahydrofuran It is apparent from the results of Table 2 that the fluorine-containing polymer of the present invention is excellent in solubility, whereas the prior fluorine segment-containing polymers have a problem in solubility.

As has been mentioned above, the present invention provides a novel fluorine-containing azo compound useful for introducing a fluorine segment into an intended site of polymer molecule. A fluorine segment can be introduced into an intended site of polymer molecule in a high efficiency by carrying out polymerization by the use of the fluorine-containing azo compound of the present invention. Thus, the present invention can contribute to the industry greatly.

What is claimed is:

1. A fluorine-containing azo compound represented by the formula:

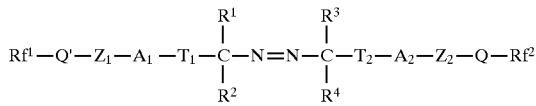   [1]

wherein $R^1$ and $R^3$ independently represent a lower alkyl group; $R^2$ and $R^4$ independently represent a lower alkyl group or a cyano group; $A_1$ and $A_2$ independently represent a lower alkylene group which may contain one or more oxygen atoms and/or an aromatic ring; $Z_1$ and $Z_2$ independently represent an ester linkage or an amido linkage; $T_1$ and $T_2$ independently represent —CONH— or a direct link; Q and Q' independently represent a fluorine-containing segment; and $Rf^1$ and $Rf^2$, independently represent a fluorine-containing alkyl group, wherein the fluorine-containing segment is represented by the formula:

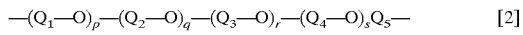   [2]

wherein $Q_1$ and $Q_4$ independently represent an alkylene group; $Q_2$ and $Q_3$ independently represent a fluorine-containing alkylene group; $Q_5$ represents an alkylene group or a fluorine-containing alkylene group; p and s independently represent 0 or a natural number; and q and r independently represent a natural number.

2. A process for producing a fluorine-containing azo compound, which comprises reacting an azo compound of the formula:

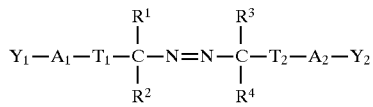   [3]

wherein $Y_1$ and $Y_2$ represent independently a carboxyl group, a hydroxyl group, an amino group or an isocyanate group; wherein $R^1$ and $R^3$ independently represent a lower alkyl group; $R^2$ and $R^4$ independently represent a lower alkyl group or a cyano group; $A_1$ and $A_2$ independently represent a lower alkylene group which may contain one or more oxygen atoms and/or an aromatic ring; $T_1$ and $T_2$ independently represent —CONH— or a direct link; with a fluorine-containing compound which has terminal groups reactive with $Y_1$ and $Y_2$ to form an ester linkage or an amido linkage, wherein the fluorine containing compound is represented by the formula:

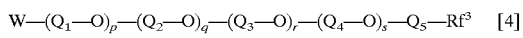   [4]

wherein $Q_1$ and $Q_4$ independently represent an alkylene group; $Q_2$ and $Q_3$ independently represent a fluorine-containing alkylene group; $Q_5$ represents an alkylene group or a fluorine-containing alkylene group; p and s independently represent 0 or a natural number; and q and r independently represent a natural number; W represents a group reactive with $Y_1$ and $Y_2$ to form an ester linkage or an amido linkage; and $Rf^3$ represents a fluorine-containing alkyl group.

3. A process for producing a polymer, which comprises polymerizing a monomer using a fluorine-containing azo compound of claim 1 as a polymerization initiator.

4. A process according to claim 3, wherein the monomer is represented by the formula:

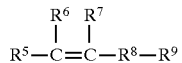   [5]

wherein $R^5$ represents a hydrogen atom, a lower alkyl group or a halogen atom; $R^6$ represents a hydrogen atom, a lower alkyl group, a halogen atom, a carboxyl group, an alkyloxycarbonyl group or a formyl group; $R^7$ represents a hydrogen atom, a lower alkyl group, a carboxyl group, an alkyloxycarbonyl group or a halogen atom; $R^8$ represents an alkylene group which may optionally have a double bond or represents a direct link; and $R^9$ represents a hydrogen atom, an alkyl group, a haloalkyl group, an aryl group, an aliphatic heterocyclic group, an aromatic heterocyclic group, a halogen atom, an alkyloxycarbonyl group, an aralkyloxycarbonyl group, a hydroxyalkyloxycarbonyl group, an aryloxycarbonyl group, an acyloxy group, a cyano group, a carboxyl group, a formyl group, an amino group, a sulfonic acid group, a carbamoyl group or a hydroxyl group.

5. An azo initiator comprising a fluorine-containing azo compound of claim 1.

6. A fluorine-containing polymer comprising, as constituents thereof, unit(s) derives from the fluorine-containing azo compound of claim 1 and those derived from a monomer.

7. A fluorine-containing polymer according to Claim 6, wherein the unit derived from the fluorine-containing azo compound is represented by the formula [1a] or [1b], or both in the case of two units being present:

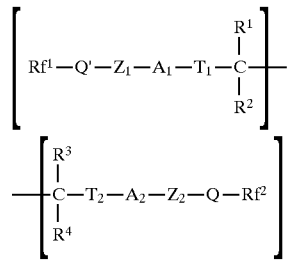

[1a]

[1b]

wherein $R^1$ and $R^3$ independently represent a lower alkyl group; $R^2$ and $R^4$ independently represent a lower alkyl group or a cyano group; Aand $A_2$ independently represent a lower alkylene group which may contain one or more oxygen atoms and/or an aromatic ring; $Z_1$ and $Z_2$ independently represent an ester linkage or an amido linkage; $T_1$ and $T_2$ independently represent —CONH— or a direct link; Q and Q' independently represent a fluorine-containing segment; and $Rf^1$ and $Rf^2$ independently represent a fluorine-containing alkyl group.

8. A fluorine-containing polymer according to claim 7, wherein the unit derived from a monomer is represented by the formula:

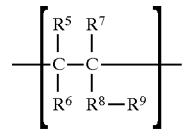   [5a]

wherein $R^5$ represents a hydrogen atom, a lower alkyl group or a halogen atom; $R^6$ represents a hydrogen atom, a lower alkyl group, a halogen atom, a carboxyl group, an alkyloxycarbonyl group or a formyl group; $R^7$ represents a hydrogen atom, a lower alkyl group, a carboxyl group, an alkyloxycarbonyl group or a halogen atom; $R^8$ represents an alkylene group which may optionally have a double bond or represents a direct link; and $R^9$ represents a hydrogen atom, an alkyl group, a haloalkyl group, an aryl group, an aliphatic heterocyclic group, an aromatic heterocyclic group, a halogen atom, an alkyloxycarbonyl group, an aralkyloxycarbonyl group, a hydroxyalkyloxycarbonyl group, an aryloxycarbonyl group, an acyloxy group, a cyano group, a carboxyl group, a formyl group, an amino group, a sulfonic acid group, a carbamoyl group or a hydroxyl group, the unit derived from the fluorine-containing azo compound is represented by the formula [1a] or [1b], or both in the case of two units being present:

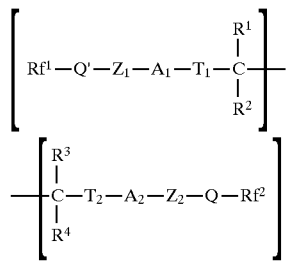

wherein $R^1$ and $R^3$ independently represent a lower alkyl group; $R^2$ and $R^4$ independently represent a lower alkyl group or a cyano group; $A_1$ and $A_2$ independently represent a lower alkylene group which may contain one or more oxygen atoms and/or an aromatic ring; $Z_1$ and $Z_2$ independently represent an ester linkage or an amido linkage; $T_1$ and $T_2$ independently represents —CONH— or a direct link; Q and Q' independently represent a fluorine-containing segment; and $Rf^1$ and $Rf^2$ independently represent a fluorine-containing alkyl group.

9. A process for preparing a coating resin composition or a painting resin composition which comprises mixing the polymer of claim 6 with a solvent.

10. A process for preparing hair cosmetics or fundamental cosmetics which comprises dissolving the polymer of claim 6 in a hydrophillic organic solvent.

* * * * *

UNITED STATES PATENT AND TRADEMARK OFFICE
CERTIFICATE OF CORRECTION

PATENT NO. : 5,847,091
DATED : December 8, 1998
INVENTOR(S) : Kazuo SHIRAKI and Nobutaka SHIMAMURA It is certified that error appears in the above-indentified patent and that said Letters Patent is hereby corrected as shown below:

Column 16, line 23, change "derives" to --derived--; and line 41, change "Aand $A_2$" to --$A_1$ and $A_2$--.

Signed and Sealed this

Twenty-third Day of November, 1999

*Attest:*

Q. TODD DICKINSON

*Attesting Officer*       *Acting Commissioner of Patents and Trademarks*